United States Patent [19]

Anderson

[11] Patent Number: 4,770,593
[45] Date of Patent: Sep. 13, 1988

[54] SAMPLE CHANGER FOR X-RAY DIFFRACTOMETER

[75] Inventor: Robert L. Anderson, Verona, Wis.

[73] Assignee: Nicolet Instrument Corporation, Madison, Wis.

[21] Appl. No.: 2,458

[22] Filed: Jan. 12, 1987

[51] Int. Cl.⁴ ............... B65G 01/00; B66C 23/00; G01N 23/20

[52] U.S. Cl. .................. 414/331; 221/13; 250/201; 378/75; 378/79; 378/208; 414/744 A; 414/225; 901/38; 901/39

[58] Field of Search .............. 901/39, 38, 31; 414/331, 404, 225, 416, 744 A; 356/244, 246; 378/208, 75, 79, 70, 71, 44, 45, 49, 204; 350/529, 530, 531, 532, 533; 221/109, 13, 210; 250/201 R

[56] References Cited

U.S. PATENT DOCUMENTS

| | | | |
|---|---|---|---|
| 3,306,471 | 2/1967 | Devol | 414/744 A |
| 3,307,036 | 2/1967 | Bouvelle | 378/75 |
| 3,353,020 | 11/1967 | Bennett et al. | 378/75 |
| 3,527,942 | 9/1970 | Roe et al. | |
| 3,920,151 | 11/1975 | Roe | |
| 4,391,387 | 7/1983 | Bayne et al. | 221/13 |
| 4,423,998 | 1/1984 | Inaba et al. | 414/744 A |
| 4,451,197 | 3/1984 | Lange | 414/744 B |
| 4,577,338 | 3/1986 | Takahashi et al. | |
| 4,582,191 | 4/1986 | Weigand | |
| 4,609,326 | 9/1986 | Roesler | 901/39 |

FOREIGN PATENT DOCUMENTS 2143199 6/1985 United Kingdom ............... 414/416

OTHER PUBLICATIONS

Advertising brochure from Nicolet Instrument Corporation entitled "The Nicolet I2 . . . Computerized Powder Diffraction for Today's Analytical Needs", 1984.

Primary Examiner—Craig E. Church
Assistant Examiner—T. N. Grigsby
Attorney, Agent, or Firm—Isaksen, Lathrop, Esch Hart & Clark

[57] ABSTRACT

A sample changer for powder X-ray diffractometry includes a cylindrical dispensing container for holding a stack of pre-test sample holders, a cylindrical receiving container for holding a stack of post-test sample holders and a changer arm which automatically picks up the topmost sample disk in the dispensing container and rotatably positions the sample disk on the sample holder stage of an X-ray diffractometer for analysis. After analysis, the changer arm removes the sample holder and releases it into the receiving container. The sample holders have a circumferential groove which coacts with semi-circular rotatable cams positioned on the distal end of the changer arm to enable the changer arm to lift and place the sample holders.

14 Claims, 3 Drawing Sheets

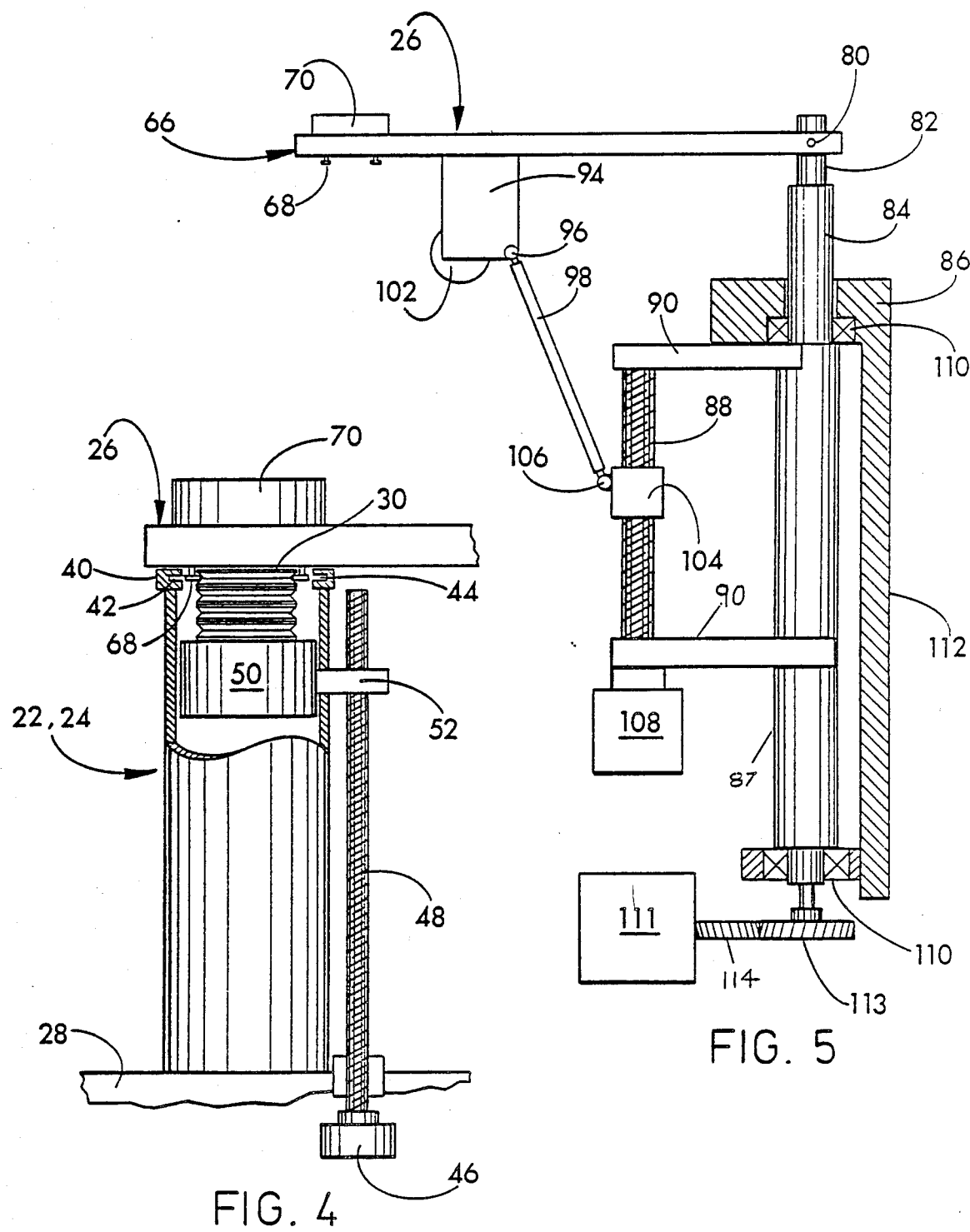

SAMPLE CHANGER FOR X-RAY DIFFRACTOMETER

TECHNICAL FIELD

The present invention is directed to sample changers and particularly to a sample changer for powder X-ray diffractometry.

BACKGROUND OF THE INVENTION

X-ray powder diffractometry is used to determine the identity of substances as well as for other types of analyses. In essence, a small collimated beam of nearly monochromatic X-rays is directed onto a polycrystalline specimen in the form of powder, producing a diffraction pattern that is recorded on film or with a counter tube. This X-ray pattern is a uniquely characteristic property resulting from the atomic arrangement of the diffracting substance. Different substances have different atomic arrangements or crystal structures; hence, no two chemically distinct substances give identical diffraction patterns.

It is generally the practice for technicians conducting routine X-ray analyses to change each sample by hand. When a large number of samples are being analyzed, such manual manipulations are time-consuming, troublesome and costly. Consequently, there is a need for an automatic sample changer which can make unattended analyses of multiple samples.

U.S. Pat. Nos. 3,527,942 to Roe, et al. and 3,920,151 to Roe each disclose an automatic sample changer in which samples are configured into a cylindrical or plate-like pellet and aligned on edge in an inclined loading ramp which gravity feeds the pellets sequentially to a sample holder. The pellets roll one at a time into a channel in the sample holder for analysis. However, the ability to automatically and efficiently change samples in powder form is not heretofore known.

SUMMARY OF THE INVENTION

The present invention provides a new and improved sample changer which dispenses powdered samples for analysis by X-ray diffractometry, and allows a plurality of samples to be dispensed under computer control with no intervention required by a user beyond loading the samples and programming the computer.

In accordance with the present invention, a sample changer for use with an X-ray diffractometer includes at least two vertical cylindrical containers, one of which, a dispensing container, holds the samples prior to test, while the other, a receiving container, holds the samples after test. A changer arm moves the holders for the samples between the dispensing and receiving containers and the X-ray analyzer test position, and is well adapted to the use of a computerized process for the automatic sequencing of the samples.

Each sample holder container has a sensing element at the top-most end which senses the presence or absence of a sample holder. If, in the case of a dispensing container, a sample holder is missing or, in the case of a receiving container, a sample holder is present in the top-most position, the sensing element activates an appropriate motor which either raises a sample holder into a position where it can be grasped by the changer arm in the case of a dispensing container, or lowers the sample holder in the case of a receiving container after an analyzed sample holder has been deposited by the changer arm.

Further objects, features, and advantages of the invention will become apparent to those skilled in the art from the following detailed description when read in conjunction with the accompanying drawings.

BRIEF DESCRIPTION OF THE DRAWINGS

FIG. 4 is a cross-sectional view of a dispensing or receiving container containing four sample holder disks for exemplification;

FIG. 5 is a side elevational view of the changer arm assembly;

DESCRIPTION OF THE PREFERRED EMBODIMENT

Figure 1:
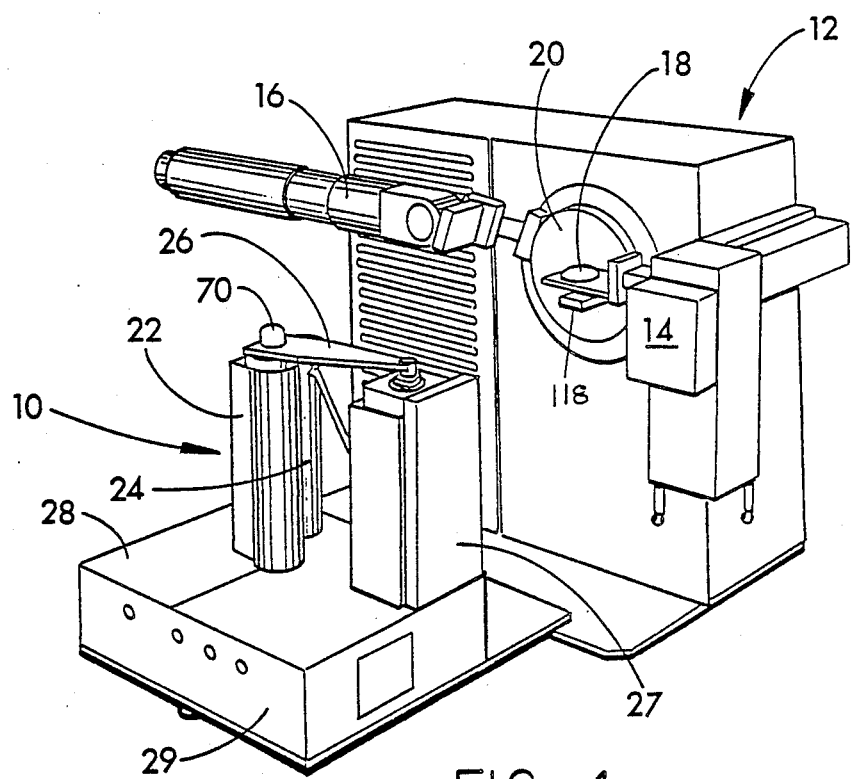
FIG. 1 is a perspective view of the sample changer of the present invention attached to an X-ray diffractometer.

The present invention will now be described with reference to the drawings, wherein like numrrals will be used for the same features throughout the figures. Although it is quite evident that the sample changer of the present invention, herein designated by numeral 10, has a variety of uses, the sample changer 10 is particularly useful in conjunction with an X-ray diffractometer referred to generally at 12 in FIG. 1.

The basic components of the diffractometer 12, which is a conventional design, include an X-ray source 14, a counter or detector 16, and a sample holder stage 18 on a goniometer element 20. A specimen or sample is centered on the stage 18 between cam wheels 19 where it may be exposed to X-ray beams generated by the source 14. During the analysis, the sample holder is rotated through a predetermined angle while the detector 16 is aligned so that it always points toward the diffracted X-ray beam. If "theta" is the angle the face of sample holder stage 18 makes with the incident X-ray beam, the detector 16 must be aligned at an angle of 2 "theta". It follows that the detector 16 must arcuately move about the axis of the rotating element 20 at twice the angular speed of the sample 18 to maintain proper alignment. Since the sample powder is randomly oriented, a certain number will always be in position such that Bragg's law is satisfied. The diffracted beams, which flash out as the sample holder rotates through the appropriate Bragg angles, are detected by the detector 16 and recorded.

Figure 2:
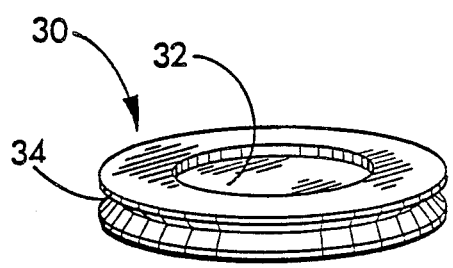
FIG. 2 is a perspective view of a sample holder disk.
Figure 3:
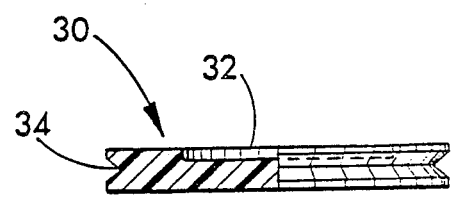
FIG. 3 is a partial cross-sectional view of the sample holder disk of FIG. 2.

The general construction of the sample changer 10 is also illustrated in FIG. 1 wherein numeral 22 refers to the dispensing container 24 refers to the receiving container 26 refers to the changer arm and 28 refers generally to the base unit. Containers 22 and 24 are preferably cylindrical in configuration and are designed to hold relatively flat, disk shaped, sample holders 30 best illustrated in FIGS. 2 and 3. An exemplary sample holder 30 is approximately 3 centimeters in diameter and 0.5 centimeters thick. The top-face portion of the sample holder 30 has a recess 32 cut into it for holding the sample powder to be analyzed. The side walls of the sample holder 30 are pinched inward to form a circumferential groove 34 to enable the cam wheels 19 on the stage 18 to engage the holder and to allow the mechanism of the changer arm 26 to pick up the sample holder, as further described below. If desired, a recess (not shown) may also be cut into the bottom portion of the sample holder 30 to minimize interference with other sample holders when the sample holders are stacked in the containers 22 and 24. The sample holders are preferably formed of a hard plastic or other suitable material which will not substantially interfere with the X-ray analysis procedure.

Referring to FIG. 4, there is illustrated, in cross-section, either a dispensing container 22 or a receiving container 24, it being understood that the two are substantially identical in construction. The containers 23 and 24 are preferably designed to hold a stack of sample holders, e.g., 49, although it is within the scope of the invention to lengthen or shorten the containers to accommodate more or less sample holders as desired. It is also within the scope of the present invention to add additional dispensing and receiving containers to the automatic sample changer 10, thus doubling the capacity of the sample changer. Both of these containers are essentially identical in size, shape and component structure and differ only in their purpose, which is dictated by commands generated by the system's controller. The container operation may be controlled, as desired, by appropriate switches generally located on a front panel 29. The containers serve as holding bins for sample holders 30 which are initially manually stacked through the opening in the top portion of the dispensing container, and may be manually removed from the receiving container after all the analyses have been completed.

Each of the containers has a sensing element 40 at its top which senses the presence or absence of a sample holder 30 at the topmost sample holder position. In the preferred embodiment, the sensing element 40 comprises a photosensor 42 and a light emitter 44. The light emitter 44 directs a beam of light toward the photosensor 42. When the light beam is unimpeded, in the case of the dispensing container 22, a motor 46 is activated which rotates a helix screw 48, to which a helix nut 52 is threaded. The helix nut 52 is attached to a shelf 50 within the container and drives the shelf upwardly as the helix screw rotates to elevate the stack of holders until the light beam path is broken, thus shutting off the motor. Preferably, the motor 46 is a direct current (D.C.) motor. When the light beam is broken or impeded in the case of the receiving container 24, the D.C. motor 46 in the base unit 28 is activated to rotate helix screw 48 in an opposite direction, lowering the shelf 50 until the light beam is sensed, which shuts off the motor 46.

By the coaction of the sensing element 40 and the motor 46, each of the containers 22 and 24 is self-controlling in that the motor 46 will be activated or deactivated depending upon whether a sample holder 30 is to be unloaded or loaded. Standard control circuitry may be implemented in a well known manner to effectuate the control of the motors 46 by the sensing elements 40.

The foregoing description of the sample holder containers will now be more particularly described with respect to the independent actions of the dispensing container 22 and the receiving container 24. The dispensing container 22 is a large upright tube that holds a plurality of sample holders 30 in stacked relation until they are ready for analysis. The photosensing element 40 at the top of container 22 registers whether or not a sample holder 30 is in position to be picked up by the changer arm 26. If a sample disk is not in position, the motor 46 is automatically activated, thus rotating the helix screw 48 to raise the shelf 50 and the stack until the beam of light in the sensing element 40 is obstructed, shutting off the motor 46 and stoping the upward movement of the shelf 50. At this point, the topmost sample holder is in a position where the changer arm 26 can pick it up for deposition onto the sample holder stage 18 of the X-ray diffractometer analyzer 12.

The receiving container 24 is identical to the dispensing container 22 except that the receiving container stores the sample holders 30 after the powdered sample on the disk has been analyzed. Like the dispensing container 22, the receiving container 24 has an optical sensing element 40 which registers when a sample container has been added to the stack. When the receiving container 24 senses the presence of a newly deposited sample holder in the topmost position, the motor 46 is activated, thus lowering the shelf 50 until a vacancy, as indicated by an intact light beam between the light emitter 44 and the photosensor 42, is created in the topmost position. This allows the changer arm 26 to place the most recent post-test sample holder 30 in the topmost position in the cylinder.

Figure 6:
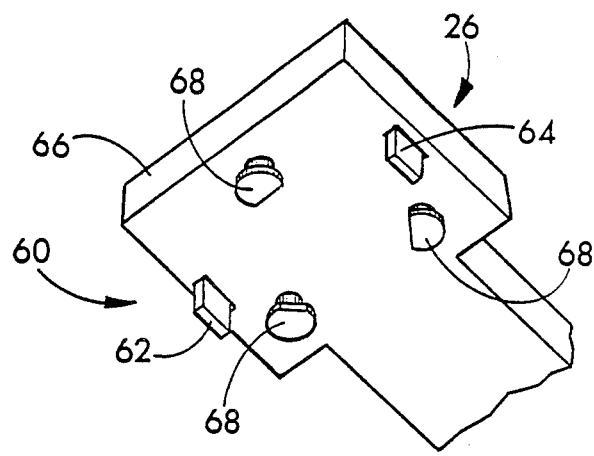
FIG. 6 is a bottom perspective view of the distal end of the changer arm of the present invention, illustrating three semi-circular sample holder gripping cams and a sample holder sensing element.
Figure 7:
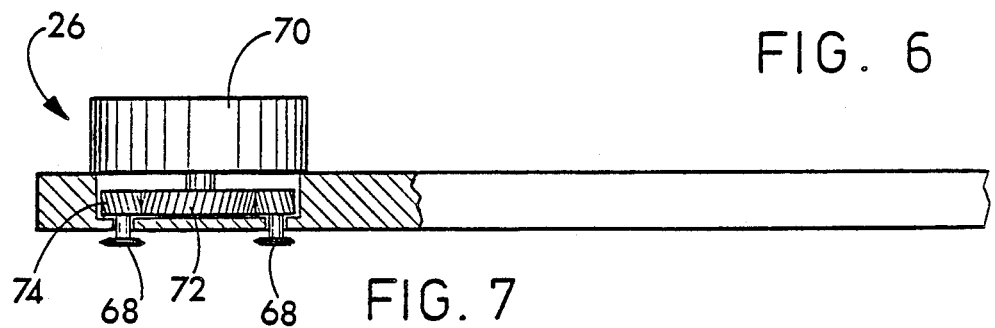
FIG. 7 is a cross-sectional view of the distal end of the changer arm of FIG. 5 illustrating the gearing mechanism of the gripping cams.
Figure 8:
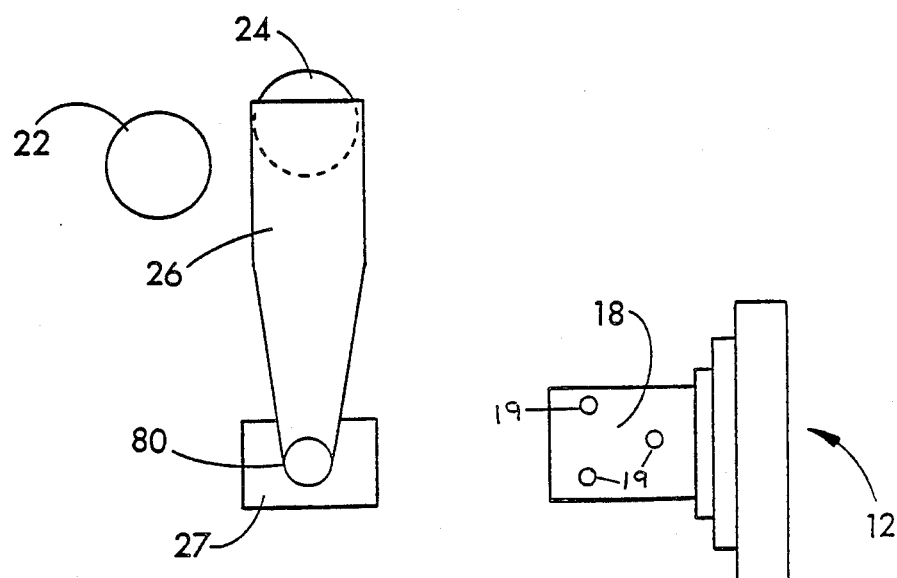
FIG. 8 is a schematic drawing showing the relationship of the changer arm to the receiving container, the dispensing container and the sample test/station of the X-ray diffractometer.

Referring now to FIGS. 5–8, the changer arm 26 is a device which physically moves sample holders from the dispensing container to the sample holder stage of the X-ray diffractometer 12 and then, after completion of the analysis, to the receiving container. The changer arm 26 is, for exemplification, approximately 9 inches long and is electrically operated by stepper motors and gears located in a changer arm base portion 27 and in the base unit 28. The activating assembly for the changer arm 26 is best shown in FIG. 5 which illustrates the changer arm and the activating assembly with the housing for the changer arm base 27 removed. The changer arm 26 is pivotally attached to the base 27 at two points. A base hinge 80 connects the proximal end of the changer arm 26 to a rotatable post 82 having an expanded column portion 84. The column 84 is journaled by bearings 110 to an upright base support 112 which includes an upper collar 86. A helix screw 88 is mounted for rotation between joining plates 90 which are attached to an expanded sleeve 87 which rotates with the post 82. The other pivotal attachment for the changer arm 26 is located at a support block 94 hinge 96 which pivotally connects the changer arm 26 to a lift lever 98. Extending outwardly on the support block 94 from the hinge 96 is an activating wheel 102. The activating wheel 102 serves to move a slide 118 on the sample holder stage 18 to allow the changer arm 26 to dispense samples onto the sample holder stage between the rotating wheels 19 on the stage. Opposite the hinge 96, the lift lever 98 is pivotally connected to a collar 104 by a pivotal collar hinge 106. The collar 104 is threaded to the helical screw 88 to move up or down on it depending on the direction of rotation of the screw. The helix screw mechanism as illustrated in FIG. 5 is preferably computer controlled and drives a stepper motor 108 a predetermined number of steps which rotate the helix screw 88 to raise and lower the arm 26 a predetermined distance. The changer arm mechanism, however, is also able to rotate about the post 82, thus enabling the changer arm 26 to rotate between the dispensing and receiving containers 22 and 24 and the sample holder stage 18, the relative positions of which are illustrated in FIG. 8.

Referring back to FIG. 5, the two contact bearings 110 are mounted in blocks attached to the upright column 112 which is attached to the structure of the base 28. The post 82, including the column 84 and sleeve 87 is mounted for rotation by contact bearings 110 and preloaded so no vertical motion takes place. A second stepper motor 111 drives a worm gear 114 which turns a gear 113 attached to the post 82. As the post 82 rotates, the changer arm 26 also rotates and thus can be positioned over the container 22 or 24 or over the sample holder stage 18. The stepper motor 111 rotates a predetermined number of steps either clockwise or counterclockwise as determined by, for example, a computer control system. By using the stepper motors 108 and 111, the vertical and horizontal positions of the end of the changer arm is known from the number of rotational steps produced by the motors so that position feedback is not required.

As illustrated in FIG. 6, a photosensing element 60, similar to the sensing element 40 of the containers 22 and 24, is mounted at the lower surface of the changer arm distal end. The photosensing element 60 comprises a light emitter 62 and a photosensor 64, the purpose of which is to determine whether or not the changer arm is grasping a sample holder 30. Also positioned on the bottom of the distal end 66 of the changer arm 26 are a plurality of, preferably three, gripping cams 68, which serve to selectively grip a sample holder 30. The gripping cams 68 are semi-circular cams, generally arranged at the vertices of an equilateral triangle. When the gripping cams 68 each have their circular side toward a sample holder 30, a ridge around each of the cams 68 engages the circumferential groove 34 around the sample holder 30, thereby holding the sample holder to the changer arm 26 for lifting. When the cams 68 have their flat sides toward a sample holder 30, as illustrated in FIG. 6, the clearance between the sample holder 30 and the cams 68 allows the sample holder to drop from the changer arm 26 under the force of gravity.

The gripping cams 68 are activated by an electric solenoid 70 which is mounted on the end of the changer arm 26, as illustrated in FIG. 7. The solenoid 70 operates a central gear 72. When the solenoid 70 is deenergized, the flat sides of the cams will face each other as shown. When energized, the solenoid 70 will cause the gear 72 to rotate approximately 22.5°, which will drive three cam gears 74, each connected to one cam, approximately 55°, at which point the gripping cams 68 will engage the circumferential groove 34 of the sample holder 30.

The operation of the dispensing and receiving containers and the changer arm are preferably controlled by a control system in the base unit 28. Such control system can include a programmable computer controller, implemented in a standard fashion, so that the movement of the stepper motors 108 and 111 and the solenoid 70 can be integrated to efficiently operate the changer arm 26.

The system may be operated by an attendant using switches on the front panel 29 of the base unit 28. With proper programming, only three control switches are necessary: the on/off switch which turns the electrical power to the changer on or off and two up/down switches which control the feed direction of the dispensing and receiving containers. Each dispensing and receiving container is preferably controlled by a separate up/down switch. If more than one dispensing and receiving container are present on the sample changer, the number of control switches will also be increased to reflect the additional containers.

Having thus described the individual features of automatic sample changer 10, the sample changer will now be described with respect to its operational sequence.

Prior to putting the automatic sample changer of the present invention into operation, the system may be programmed to interface with a particular X-ray diffractometer and to indicate the number of samples to be stacked in the dispensing container 22. The samples are then loaded into the dispensing container by the operator. As sample holders are loaded into the dispensing container, the shelf 50 will move downwardly until the sensor 40 determines that the top end of the dispensing tube is clear of sample holders. The sample holders will remain in the dispensing container 22 for storage until the data collection program of the X-ray diffractometer activates the changer arm.

Prior to X-ray diffractometer activation, the changer arm is positioned at a "zero" position for calibration. At the "zero" or home position, the changer arm is located over the sample holder stage 18 on the X-ray diffractometer 12. The sample changer is calibrated correctly when the changer arm 26 can be freely raised and lowered without interfering with the X-ray diffractometer 12. The sample changer 10 is preferably secured to the base of the X-ray diffractometer 12 by any suitable means, such as screws, so that the position of the sample changer and spectrometer remain fixed with respect to each other. The changer arm 26 can now be positioned over the dispensing container 22 and lowered to a position immediately over the top sample holder 30 in the dispensing container 22. At this point, the solenoid 70 is energized, rotating the cams 68 to grip the circumferential groove 34 of the sample holder 30. The changer arm 26 is then raised to a position slightly above the dispensing container 22. The photosensing element 64 on the changer arm 26 automatically determines whether the sample holder 30 is in position. If not, the process is repeated until the changer arm 26 engages the sample holder 30.

After lifting a sample holder 30, the changer arm 26 is rotated to the sample holder stage 18 of the X-ray diffractometer 12. The positioning of the containers 22 and 24 and the sample holder stage 18 with respect to the changer arm is illustrated in FIG. 8. The sample holder stage 18 is preferably equipped with sensing elements (not shown) to determine whether a sample is present for testing. It is also generally preferred for the sample holder stage 18 to employ a triangular arrangement of circular cam wheels 19 to grip and rotate a sample holder 30 via the circumferential groove 34. A spring holds the sample holder stage cam wheels 19 against the sample holder 30 during the operation of the diffractometer. A cam drive wheel slide 118 on the diffractometer is enaged by the wheel 102 mounted on the changer arm 26 when the changer arm 26 moves into position to deposit or retrieve a sample holder. When the slide 118 is engaged by the wheel 102, the drive cam wheels 19 on the stage 18 release their grip on the sample holder and allow the removal of the sample holder. As the arm 26 lifts, the wheel 102 releases the slide 118, allowing the cam wheels 19 to move inwardly and engage a sample holder left on the stage.

After the sample holder is released from the changer arm 26 onto the stage 18, the arm is raised and rotated approximately 90° counterclockwise while the sample is evaluated. After evaluation, the changer arm 26 rotates back over the sample holder, lowers, and picks up the analyzed sample holder 30 by activating the solenoid 70. As noted above, engagement of the wheel 102 to the slide 118 releases the drive cam wheels 19 from the sample holder. The changer arm 26 then raises and rotates to the receiving container 24, lowers and releases the sample holder 30 by de-energizing the solenoid. As the sample disk 30 drops to the topmost position of the receiving container, it breaks the light beam on the sensing element 40, thus activating the motor 46 to lower the shelf 50 until the light beam of the sensing element 40 is again made intact. At this point, the motor 46 is deactivated and the shelf 50 stops movement. The changer arm 26 then raises, rotates to the dispensing container, lowers, picks up another sample holder 30 and the sequence is repeated.

If the arm does not pick up a sample after two tries, the arm preferably will stop in an up position and an error message will be displayed to the operator.

The invention herein described thus is capable of being used with computer control to dispense sample holders automatically for analysis by an X-ray diffractometer. Samples may be dispensed with no intervention required by a technician beyond loading the samples and running the X-ray diffractometer. The sample changer allows automation of sample handling for routine analysis of a large number of samples and can be used without any significant modification of the X-ray diffractometer.

It is understood that the invention is not limited to the particular embodiments disclosed herein, but embraces all such modified forms thereof as come within the scope of the following claims.

What is claimed is:

1. In an analyzer, such as an X-ray diffractometer, a sample changer for positioning one of a plurality of stackable sample holders in a predetermined position in relation to the analyzer, comprising:
   (a) a base portion;
   (b) at least one dispensing container attached to the base portion for holding a plurality of sample holders in stacked relation prior to analysis by the analyzer, the dispensing container having an open top end and including means at the top end for sensing the presence of a sample holder at the topmost sample holder position, and further including a first movable shelf positioned within the dispensing container for supporting the stack of sample holders, and means for raising and lowering the first movable shelf to raise or lower the stack of sample holders within the dispensing container, such that the stack of sample holders within the dispensing container may be raised as necessary until the means at the top of the dispensing container senses the presence of a sample holder at the topmost position;
   (c) at least one receiving container attached to the base portion for holding a plurality of sample holders in stacked relation after analysis by the analyzer, the receiving container having an open top end and including means at the top end for sensing the absence of a sample holder at the topmost sample holder position, and further including a second movable shelf positioned within the receiving container for supporting the stack of sample holders, and means for raising and lowering the second shelf to raise or lower the stack of sample holders within the receiving container, such that the stack of sample holders within the receiving container may be lowered as necessary until the means at the top of the receiving container senses the absence of a sample holder at the topmost position; and
   (d) a changer arm having a fixed length for selectively moving to and from the positions of the top of the dispensing container, the top of the receiving container, and a position remote from the containers where a sample held by a sample holder can be analyzed by the analyzer and having means thereon for selectively grasping and releasing a sample holder such that the changer arm can grasp a sample holder at the top of the dispensing container and move it to the analyzer for analysis, and thence move the analyzed sample holder from the analyzer to the top of the receiving container and deposit it therein.

2. The sample changer of claim 1 wherein the means for sensing the presence of a sample holder at the top position in the dispensing container is an optical sensor and wherein the means for sensing the absence of a sample holder at the top position in the receiving container is an optical sensor.

3. The sample changer of claim 1 wherein the changer arm has a proximal end and a distal end, wherein the base portion includes an upright post rotatably attached thereon, the proximal end of the changer arm being pivotably attached to the upright post to pivot up and down in a vertical plane and being rotatable with the post such that the distal end of the changer arm can rotate horizontally, and including means for selectively rotating the post and means for selectively pivoting the changer arm upwardly and downwardly about its pivotal attachment to the post.

4. The sample changer of claim 3 wherein the means for selectively rotating the post includes a stepper motor connected to the post to rotate the same; and wherein the means for selectively raising and lowering the changer arm about its pivot includes a helical screw and a stepper motor connected to drive it, a collar threaded to the helical screw to move up and down on the same as the screw is rotated, and a lift lever pivotally connected to the collar and pivotally connected to the changer arm such that as the collar is driven upwardly when the helical screw turns in one direction, the changer arm will be raised, and when the collar is driven downwardly as the helical screw is turned in the other direction, the changer arm will be lowered.

5. The sample changer of claim 1 wherein the changer arm has a proximal end and a distal end, and the means for grasping a sample holder includes at least three rotatable semi-circular cams, each cam having a sharp edged circular portion and a flat portion, the cams mounted to a lower surface of the distal end of the changer arm and adapted to rotate between a position in which the circular portion of the cams faces inwardly and a position in which the flat portions of the cams faces inwardly, such that the devices can selectively engage and release a disc shaped sample holder which has a circumferential groove in its side.

6. The sample changer of claim 1 wherein the means for raising or lowering the shelf of the dispensing container comprises a helix screw mounted for rotation adjacent the container, a helix nut attached to the shelf and threaded to the helix screw to be driven upwardly or downwardly as the screw is rotated, and an electric motor connected to the helix screw to selectively rotate the same in one direction or the other, and wherein the means for raising or lowering the shelf in the receiving container includes a helix screw mounted for rotation adjacent to the receiving container, a helix nut attached to the shelf and threaded to the helix screw to be driven upwardly or downwardly as the screw is rotated, and an electric motor connected to the helix screw to selectively rotate the screw in one direction or the other.

7. The sample changer of claim 5 wherein the changer arm includes a solenoid attached to the distal end of the changer arm and connected to the semicircular cams and electrically energizable to rotate the semicircular cams selectively between their two positions.

8. The sample changer of claim 1 wherein the changer arm has a proximal end and a distal end, and including an optical sensor mounted at the distal end of the changer arm for sensing the presence of a sample holder at a position wherein it can be grasped by the means for grasping a sample holder on the changer arm means.

9. The sample changer of claim 8 wherein the optical sensor includes a light beam emitter mounted to the changer arm on one side of the position where a sample holder may be grasped and a photosensor mounted to the changer arm on the other side of the position where a sample holder may be grasped.

10. A sample changer for moving sample holders of the type having a substantially flat disk shaped body with a circumferential side having a groove therein, the sample changer comprising:
(a) a base having an upright post mounted for rotation and means for selectively driving the post in rotation;
(b) a changer arm having a distal end and a proximal end and pivotally attached at its proximal end to the rotatable post;
(c) means connected to the changer arm for rotating the changer arm selectively upwardly or downwardly about its pivotal connection to the rotatable post; and
(d) at least three semicircular cams mounted to the lower surface of the changer arm at its distal end, each semicircular cam having a sharp edged circular portion adapted to fit into the groove on the peripheral edge of a sample holder and a flat portion, the semicircular cams arranged to rotate from a position in which the circular portions of the cams face inwardly and can engage the walls of the circumferential groove of a sample holder between the semicircular cams to hold the sample holder, and having a second position of the cams in which the cams are rotated to a position in which the flat portions of the cams face inwardly such that a sample holder between the cams is released by the cams, and further including means for selectively rotating the cams between the position in which the flat portion of the cams face inwardly to the position in which the circular portions of the cams face inwardly.

11. The sample changer of claim 10 wherein the means for selectively rotating the post includes a stepper motor connected to the post to rotate the same; and means for selectively raising and lowering the changer arm about its pivot which comprise a helical screw and a stepper motor connected to drive it, a collar threaded to the helical screw to move up and down on the same as the screw is rotated, and a lift lever pivotally connected to the collar and pivotally connected to the changer arm such that as the collar is driven upwardly when the helical screw turns in one direction, the changer arm will be raised, and when the collar is driven downwardly as the helical screw is turned in the other direction, the changer arm will be lowered.

12. The sample changer of claim 10 wherein the means for selectively rotating the cams comprises a solenoid attached to the distal end of the changer arm and connected to the semicircular cams and electrically energizable to rotate the semicircular cams selectively between their two positions.

13. The sample changer of claim 10 including an optical sensor mounted at the distal end of the changer arm for sensing the presence of a sample holder at a position where it can be grasped by the rotatable cams.

14. The sample changer of claim 13 wherein the optical sensor includes a light beam emitter mounted to the changer arm on one side of the position where a sample holder may be grasped by the cams and a photosensor mounted to the changer arm on the other side of the position where a sample holder may be grasped.

* * * * *